US006794125B1

(12) United States Patent
Wishart

(10) Patent No.: US 6,794,125 B1
(45) Date of Patent: Sep. 21, 2004

(54) METHOD FOR ASSESSING FOWL SPERM QUALITY

(75) Inventor: Graham John Hardman Wishart, Angus (GB)

(73) Assignee: University of Abertay Dundee, Dundee (GB)

( * ) Notice: Subject to any disclaimer, the term of this patent is extended or adjusted under 35 U.S.C. 154(b) by 78 days.

(21) Appl. No.: 10/110,132

(22) PCT Filed: Oct. 3, 2000

(86) PCT No.: PCT/GB00/03772
§ 371 (c)(1),
(2), (4) Date: Jul. 9, 2002

(87) PCT Pub. No.: WO01/27616
PCT Pub. Date: Apr. 19, 2001

(30) Foreign Application Priority Data

Oct. 8, 1999 (GB) .............................. 9923768

(51) Int. Cl.[7] .................................. A01N 1/02
(52) U.S. Cl. ................. 435/2; 435/4; 435/18; 435/29
(58) Field of Search .............................. 435/2, 29, 18, 435/4; 119/174

(56) References Cited

U.S. PATENT DOCUMENTS 5,434,057 A * 7/1995 Dorian ........................ 435/18

OTHER PUBLICATIONS

G.J. Wishart and L.K. Wood, "Evaluation of Tetrazolium Reduction Assays For Assessing Poultry Sperm Metabolism and Predicting Fertilizing Ability," World Poultry Science Assoc., vol. I, pp 310–311 , (1994).
D.M. Cooper, J.G. Rowell, "Relations Between Fertility, Embryonic Survival and Some Semen Characteristics in the Chicken," Poultry Science, 37, pp 699–707 (1958).
G.F. Barbato, P.G. Cramer, R. H. Hammerstedt, "A Practical In Vitro Sperm–Egg Binding Assay That Detects Subfertile Males," Biology of Reproduction, 58(3):686–99 (1998).
S.F. Bilgili, J.A. Renden, K.J. Sexton, "Fluorometry of Poultry Semen: Its Application in the Determination of Viability, Enzyme Leakage, and Fertility," Poultry Science 64:1227–1230 (1985).
D. Chaudhuri, G.J. Wishart, P.E. Lake, O. Ravie, "Predicting The Fertilising Ability of Avian Semen: Comparison Of A Simple Colourimetric Test With Other Methods For Predicting The Fertilising Ability of Fowl Semen," British Poultry Science, 29:847–851 (1988).
D.P. Froman, D.J. McLean, "Objective Measurement of Sperm Motility Based Upon Sperm Penetration of Accudenz," Poultry Science 75:76–784 (1996).

D.P. Froman, A.J. Feltmann, D.J. McLean, "Increased Fecundity Resulting from Semen Donor Selection Based Upon In Vitro Sperm Motility," Poultry Science 76:73–77 (1997).
David P. Froman, Allen J. Feltmann, "Sperm Mobility: A Quantitative Trait of the Domestic Fowl (*Gallus domesticus*)," Biology of Reproduction 58:379–384 (1998).
P.E. Lake, J.M. Stewart, "Artificial Insemination in Poultry," Ministry of Agriculture, Fisheries and Food, Bulletin 213, pp 30–32 (Appendix A—"The Examination of the Morphology of Spermatozoa of Domestic Fowl").
C.D. McDaniel, J.L. Hannah, H.M. Parker, T.W. Smith, C.D. Schultz, C.J. Zumwalt, "Use of a Sperm Analyzer for Evaluating Broiler Breeder Males. I. Effects of Altering Sperm Quality and Quantity on the Sperm Motility Index," Poultry Science 77:888–893 (1998).
Tim Mosmann, "Rapid Colorimetric Assay for Cellular Growth and Survival: Application to Proliferation and Cytotoxicity Assays" Journal of Immunological Methods, 65:55–63 (1983).
Dominic A. Scudiero, Robert H. Shoemaker, Kenneth D. Paull, Anne Monks, Siobhan Tierney, Thomas H. Nofziger, Michael J. Currens, Donna Seniff, Michael R. Boyd, "Evaluation of a Soluble Tetrazolium/Formazan Assay for Cell Growth and Drug Sensitivity in Culture Using Human and Other Tumor Cell Lines," Cancer Research 48:4827–4833 (1988).
L. Robertson, Y.I. Wilson, C. Lindsay and G.J. Wishart, "Evaluation of Semen From Individual Male Domestic Fowl by Assessment of Sperm: Perivitelline Interaction in vitro and in vivo," British Poultry Science 39:278–281 (1998).
H.R. Wilson, N.P. Piesco, E.R. Miller, W.G. Nesbeth, "Prediction of the Fertility Potential of Broiler Breeder Males," World Poultry Science Journal, vol. 35:91–118 (1979).
G.J. Wishart, "Maintenance of ATP Concentrations in and of Fertilizing Ability of Fowl and and Turkey Spermatozoa in vitro," Journal of Reproduction & Fertility Ltd., 66:457–462 (1982).
G.J. Wishart, "Quantitation of the Fertilising Ability of Fresh Compared With Frozen and Thawed Fowl Spermatozoa," British Poultry Science 26:375–380 (1985).
G.J. Wishart, "Physiological Changes in Fowl and Turkey Spermatozoa During in vitro Storage," British Poultry Science 30:443–454 (1989).

(List continued on next page.)

Primary Examiner—Leon B. Lankford, Jr.
(74) Attorney, Agent, or Firm—Drinker Biddle & Reath LLP

(57) ABSTRACT

A method of assessing sperm viability by measuring the ability of the sperm to reduce a tetrazolium dye and allowing color development over a range of weakly acidic pHs.

6 Claims, 5 Drawing Sheets

OTHER PUBLICATIONS

Graham J. Wishart, "Techniques for Semen Quality Determination," Third International Symposium on Turkey Reproduction, (1993).

G.J. Wishart, "Vaginal Sperm Transport and Sperm Selection," World Poultry Science Assoc. vol. II 161–165 (1994).

G. J. Wishart, Frances H. Palmer, "Correlation of the Fertilising Ability of Semen from Individual Male Fowls with Sperm Motility and ATP Content," British Poultry Science 27:97–102 (1986).

Graham J. Wishart, "New Approaches to Evaluating Male and Female Fertility," First International Symposium on the Artificial Insemination of Poultry, pp 207–223 (1994).

Chaudhurt, D. and Wishart, G.J., "Predicting the fertilising ability of avian semen: the development of an objective colourimetric method for assessing the metabolic activity of fowl spermatozoa", British Poultry Science, vol. 29, pp 837–845 (1988).

Plumb, J.A., et al., "Effects of the pH dependence of 3–(4,5–dimethylthiazol–2–yl)–2,5–diphenyltetrazolum bromide–formazan absorption on chemosensitivity determined by a novel tetrazolium based assay," Cancer Research, vol. 49, No. 16, Aug. 15, 1989.

* cited by examiner

METHOD FOR ASSESSING FOWL SPERM QUALITY

This application is the U.S. National Phase Application of PCT International Application No. PCT/GB00/03772 filed Oct. 3, 2000.

This invention relates to a method of determining spermatozoa qualities, and is particularly useful for determining the viability and fertilising ability of avian spermatozoa.

DESCRIPTION OF THE RELATED ART

Methods for assesing the quality of spermatozoa from domestic fowl and other animals, and estimations of their value as predictors of sperm fertilizing ability have been established for many decades (Cooper and Rowell, 1958; Wilson et al., 1979).

Earlier tests (Cooper and Rowell, 1958; Wilson et al., 1979) were perceived to be highly subjective, involving operator-dependent 'scoring' of a particular sperm parameter, with poor agreement between operators. More recently, this criticism has been answered by the introduction and application of a range of objective tests of chicken sperm quality (Bilgilli and Renden, 1985; Wishart and Palmer 1986; Chaudhuri and Wishart, 1988; Froman and McLean, 1996; Barbato et al., 1997). These tests have additionally shown that sperm quality in individual domestic fowl is a 'trait' which is repeatable between ejaculates in the short and longer term and can be linked to fertilizing ability (Wishart and Palmer, 1986; Chaudhuri et al., 1988; Froman et al., 1997; 1998).

A limitation of these objective tests of sperm quality is that they require laboratory facilities such as centrifuges and/or lack the robustness required for use 'on the farm'. The INT-tetrazolium dye test introduced by Chaudhuri and Wishart (1988) is relatively robust, and its outcome is easily interpreted as the intensity of colour produced by spermatozoa during a short incubation. INT-reduction was also strongly correlated with other tests of sperm 'quality', including their fertilizing ability (Chaudhuri et al., 1988). However, reagents involved in the test are unstable and some (e.g. cyanide) are highly toxic. An additional disadvantage is that samples require to be centrifuged before they are sufficiently optically clear to be read with a colorimeter. These problems have limited the practical applicability of the INT-reduction assay.

BRIEF SUMMARY OF THE INVENTION

The present invention provides a method of assessing sperm quality comprising determining whether (and optionally, to what extent) the sperm being assessed can reduce a tetrazolium dye, wherein the dye reduction is determined by monitoring colour changes at a pH above 4.0.

The tetrazolium dye is preferably MTT, which can be added to the sperm in the reaction mixture, or vice versa.

The reaction between the sperm and the dye is preferably carried out for about 1 hr at 37–40° C., and preferably at near neutral pH such as pH 6–8, e.g. pH 7.4.

The method preferably includes the step of adding a solubilizing agent such as a detergent such as SDS, or some other agent capable of solubilizing the sperm cells. Solubilizing the sperm cells or otherwise releasing their contents enables colorimetric assessment of the extent of reduction of the tetrazolium dye without centrifugation of the reaction mixture. The solubilizing agent conveniently also stops the reaction.

The colorimetric assessment of dye reduction is preferably carried out as a separate step in slightly more acidic conditions than the reaction of the dye with the sperm, such as pH 5–7 and in an especially preferred embodiment the colorimetric assessment of the dye reduction is carried out at around pH 6.

In a preferred embodiment the invention provides an assay comprising exposing spermatozoa to a tetrazolium dye (preferably MTT), solubilizing the spermatozoa to release their contents into the reaction mixture, and measuring the colour change in the reaction mixture as a result of the reduction of the tetrazolium dye, wherein at least some of the steps are carried out at a pH above pH 4.0, and typically at around pH 6.0.

The results of the colorimetric measurement of the dye reduction can be quantified against a standard of known sperm quality assayed by other means.

The sperm quality assessed is typically viability, but indicators of fertilizing ability and other characteristics of the sperm may be obtained from the colourimetric assessment of the dye reduction.

The sperm is typically avian sperm, but the method is suitable for use on other types of sperm, e.g. mammalian sperm.

Certain embodiments of the invention avoid the need for unstable and toxic reagents such as cyanide and/or the requirement for laboratory facilities like centrifuges. The addition of a reagent such as SDS clears the sperm suspension sufficiently for direct reading of the optical density of the colour produced, thereby enabling a test that can be performed on farm premises without laboratory facilities.

BRIEF DESCRIPTION OF THE DRAWINGS

Examples of the present invention will now be described by way of illustration and with reference to the following drawings.

DETAILED DESCRIPTION OF THE INVENTION

Materials and Methods for Examples 1–5.
Birds and Semen Collection

Males were an ISA Brown commercial cross, aged between 25 and 40 weeks. They were fed a breeders ration ad libitum and kept on a 14 h photoperiod. For birds in routine use, semen was collected (Lake, 1957) twice-weekly. The semen was diluted 4-fold in NaCl/TES (Chaudhuri and Wishart, 1988) and incubated aerobically for up to 2 h before use in a shaking water bath at 30° C.
Assays INT-tetrazolium reduction was carried out as described by Chaudhuri and Wishart (1988), except that, as required, the Triton X-100/HCl reagent was replaced with 10% SDS/0.01 MHCl at pH 6.0 (see Table 1). MTT-reduction was carried out in an assay volume of 1.2 ml at 37° C. The final assay protocol is shown in Table 1, although variations in the constituents, described in the Results Section, were made without diminishing the efficacy of the assay. Optical densities (OD520 for INT-formazan; OD520 for MTT formazan) were measured in a CO colorimeter (Cambridge Instruments, Cambridge).

INT-formazan production was assessed as before (Chaudhuri and Wishart, 1988); MTT-formazan using the molar extinction coefficient of 17.7. Sperm concentration was estimated by haemocytometer counts and by light scattering at OD550.
Statistical Analyses All statistical analysis was done using MINITAB 10 for Windows.

TABLE 1

MTT reduction assay for domestic fowl spermatozoa

| Stock solution | Volume In assay (ml) | Final conc'n in assay mixture (mM) |
|---|---|---|
| 150 mM NaCl with 20 mM TES, pH 7.4 | 0.90 | 123.8 |
| 100 mM Glucose | 0.10 | 9.2 |
| 4 mM MTT | 0.05 | 0.18 |
| 4-fold diluted semen | 0.04 | |
| Total volume | 1.09 | |

Procedure:
1. The assay constituents apart from MTT were mixed thoroughly in a test tube.
2. The mixture was equilibrated in a water bath at 37° C. and MTT was added and mixed thoroughly.
1. After one hour the reaction was stopped by the addition of 200 l of 10% SDS in 0.01 mol/l HCl pH 6.0, mixed and allowed to stand at room temperature for 15 minutes.
4. The absorbency was measured on a CO calorimeter at 570 nm.

Results

Example 1

Solubilisation of INT Assay Sperm Suspensions

Figure 1:
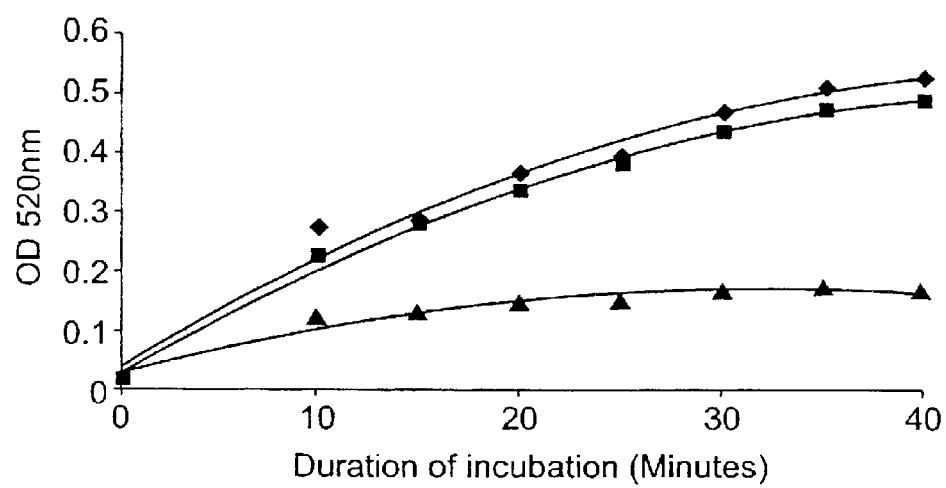
FIG. 1 shows the optical densities developed during an INT-tetrazolium assay following solubilisation with Triton-HCl, then centrifugation (triangles: $y=0.0002x^2+0.11x+0.012$; $R^2=0.96$); solubilisation with 10% SDS-0.1 mol/l HCl, then centrifugation (squares: $y=0.0002x^2+0.022+0.010$; $R^2=1.0$); and solubilisation with SDS-HCl, without centrifugation (diamonds: $y=0.0002x^2+0.023+0.020$; $R^2=1.0$).

FIG. 1 shows the optical densities developed during incubation of a sample of 10 l of semen (containing approximately 40 million spermatozoa) under the standard INT assay conditions, with solubilisation of the sperm suspensions by 10% SDS in 0.1 mole/l HCl as well as by Triton-HCl. Differences between the latter two sets of figures were not significant (Paired t-test; t=0.00231; n=8). The correlation coefficients for the Triton-solubilised samples and the SDS-solubilised samples, before and after centrifugation, were 0.98 and 0.97, respectively. Regression of the SDS-solubilised samples before centrifugation (x) and those after centrifugation (y) gave the equation y=0.940x−0.005 ($r^2$=0.994).

For 10 replicate samples treated in the same way for 20 min incubation, the mean±SD OD520 values for Triton-solubilised (+centrifugation) and SDS-solubilised (−then+ centrifugation) were 0.128±0.016, 0.114±0.009 and 0.068±0.015, respectively, and the corresponding coefficients of variation were 12.5, 7.89 and 22.06, respectively. The OD520 of Triton-solubilised samples was 46.9% of SDS-solubilised samples before centrifugation and 40.4% of SDS-solubilised samples after centrifugation. The mean loss of OD520 in the SDS-solubilised samples following centrifugation was 10.93%, but this increased to 14.2% and 41% when 15 and 20 l semen was used and was >50% when more spermatozoa were added to the assay.

Increasing the concentration of SDS in the solubilisation reagent beyond 10% did not give greater optical clarity, since the solutions became more viscous and centrifugation had no effect.

Thus solubilisation of sperm suspensions in the INT-reduction assay with 10% SDS in 0.1 mol/l HCl solubilised more than twice the amount of formazan and, furthermore, produced optically clear solutions in which the OD520 could be read without centrifugation.

Example 2

Assay with MTT

In the standard Triton-solubilised assay, around 44% more colour was developed by MTT reduction (at OD520) compared to that of INT (at OD520) at the same concentration. When 10% SDS in 0.1 mol/l HCl was used to solubilise the formazan product, the colour produced by MTT formazan was quenched. However, when the pH of the solution was raised to about pH 6.0 by addition of any suitable alkaline product e.g. NaOH, this colour was restored. Indeed, if 10% SDS in 0.01 mol/l HCl at pH 6.0 MTT-formazan colour development was good and the sperm suspensions solubilised efficiently: when 10 l semen was used in the assay, the loss of OD520 after centrifugation was only 2.2% (mean of 2 results). This increased to 4.0 and 6.7% when 15 and 20 l semen were used, respectively.

A modification to this protocol was made to determine the most effective pH for colour development; in the modified protocol, sperm was added to reaction mixtures of different concentrations of HCl, and therefore different pH and the resultant colour was read off on a spectrophotometer. The results were as follows:

TABLE 2

| pH–OD570 |
|---|
| 7.25–0.25 |
| 7.05–0.22 |
| 6.03–0.21 |
| 4.67–0.18 |
| 3.25–0.07 |
| 2.83–0.05 |
| 2.23–0.10 |
| 2.02–0.05 |

Thus, at pH of less than 5, the purple MTT formazan (purple) colour at 570 nm, and below pH 4, the colour disappears rapidly.

An acidic pH is preferred in order to solubilise the suspension, but need not be added if the OD is to be measured only semi-quantitatively, and the pH is preferably kept in a range of pH 5–7.4 for colour development.

Example 3
Effect of KCN, PMS, MTT and Calcium on INT- and MTT-reduction Assays The addition of 20 nmol KCN to the MTT-reduction assay above increased formazan production by only 13.8% and raising the cyanide content of the assay mix up to 5-fold increased this to a maximum of 31%. Conversely, during a 60-min assay, the addition of 2 nmol KCN to an INT-reduction assay increased the colour production 4.2-fold more than the effect of a similar addition to an MTT-reduction assay performed under the same conditions.

The addition of 9.9 nmol PMS increased the rate of MTT-formazan production by 22.9% and increasing the amount of PMS by up to three-fold only reduced the rate of formazan production.

The addition of 200 nmol MTT to the assay increased the rate of formazan production by 20% compared to 100 nmol and further increases in MTT did not increase the assay rate further.

The addition of 4 mol calcium chloride to the MTT assay only increased the rate of MTT-formazan production by 5.7% (mean of 6 assays).

Figure 2:
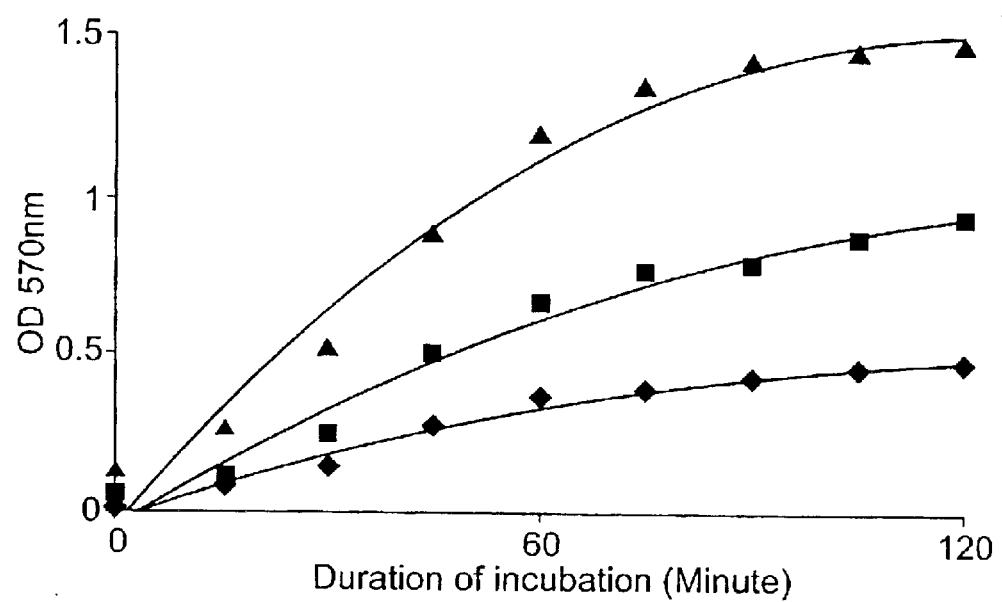
FIG. 2 shows the development of MTT-formazan colour during incubation at 37° C. with 10 (diamonds), 20 (squares) and 40 (triangles) l of the same sample of semen. Colour development is linear over 60 min: where $y=OD_{570}$ and x=incubation time in min. the regression equations are $y=0.0061x-0.016$ ($R^2=0.99$), $y=0.0113x-0.034$ ($R^2=0.97$) and $y=0.0191x+0.01$ ($R^2=0.99$) for 10, 20 and 40 l samples, respectively.

Example 4
Effect of Sperm Concentration and Time of Incubation on MTT-reduction Assay The development of colour during incubation of samples with different sperm concentrations is shown in FIG. 2. Within the range of semen volumes of 10 to 40 l (approximately 40 to 160 million spermatozoa), the assay showed a linear development of colour over 60 min. The rates of colour development over this period, at 0.37, 0.68 and 1.15 OD units per h, were highly correlated with the semen volume added to the assay (r=0.96).

Figure 3:
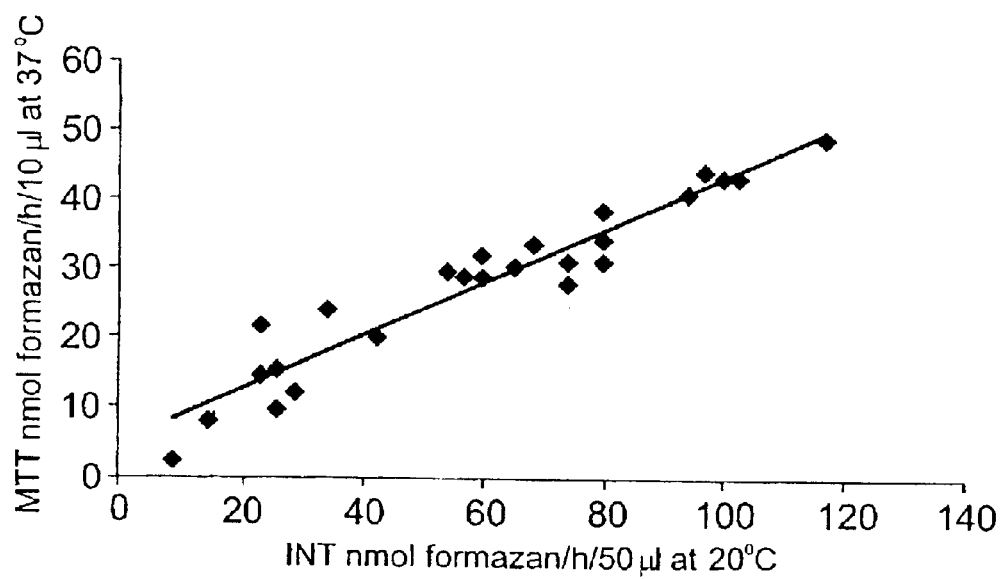
FIG. 3 shows correlation, in samples of semen from 25 individual male domestic fowl, between INT-formazan produced per h in the standard INT-reduction assay (by 50 l semen at 20° C.) and MTT-formazan produced in the standard MTT-reduction assay (by 50 l semen at 20° C.). MTT-formazan=039 INT-formazan+4.81; $R^2=0.92$).
Figure 4:
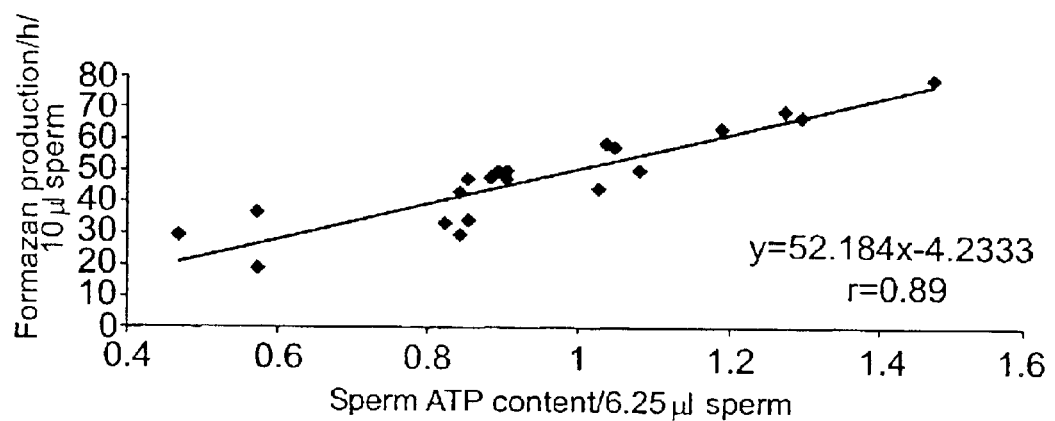
FIG. 4 shows the relationship between MTT reduction potential and sperm ATP content in spermatozoa from individual males. The relationship shown is $y=52.2x-4.2$; r=0.89; n=21.
Figure 5:
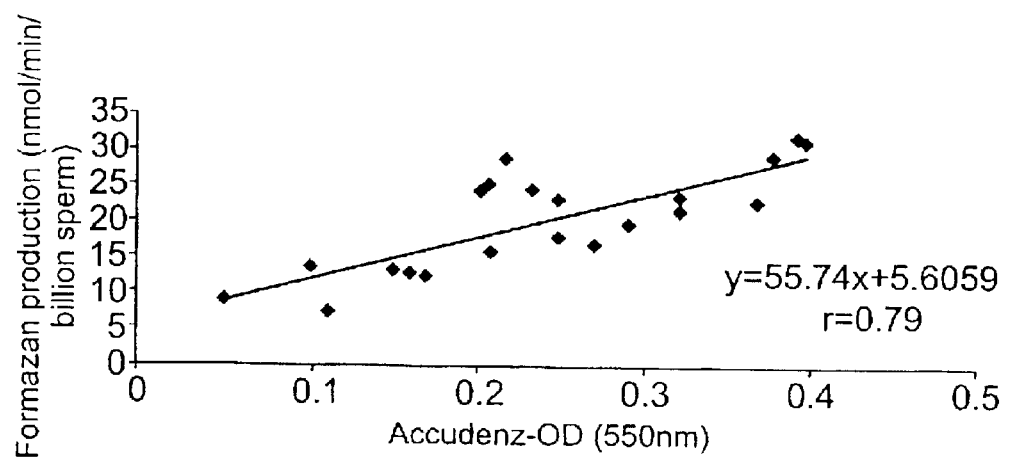
FIG. 5 shows the relationship between MTT reduction potential and sperm mobility, measured as the ability of spermatozoa to penetrate a solution of Accudenz, in spermatozoa from individual males. The relationship shown is y=56x+5.6; r=0.76; n=21.
Figure 6:
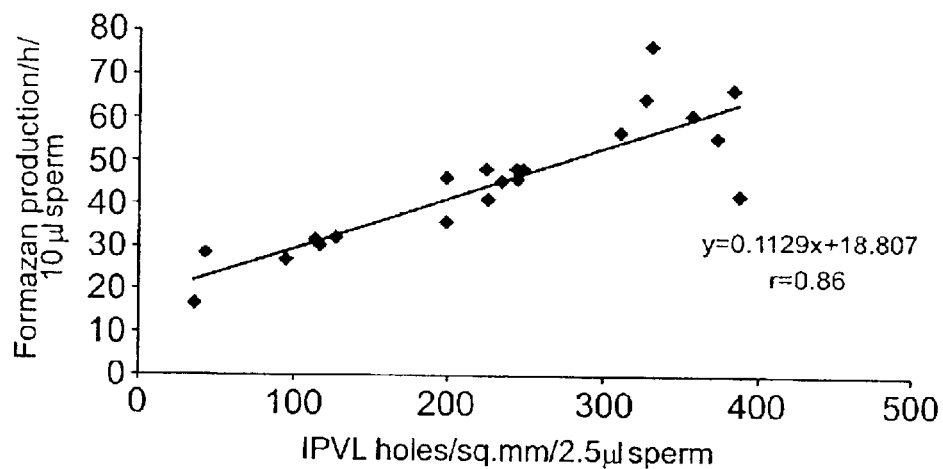
FIG. 6 shows the relationship between MTT reduction potential and the ability of spermatozoa to hydrolyse holes in the inner perivitelline layer in vitro in spermatozoa from individual males. The relationship shown is y=0.11x+19; r=0.86; n=21.
Figure 7:
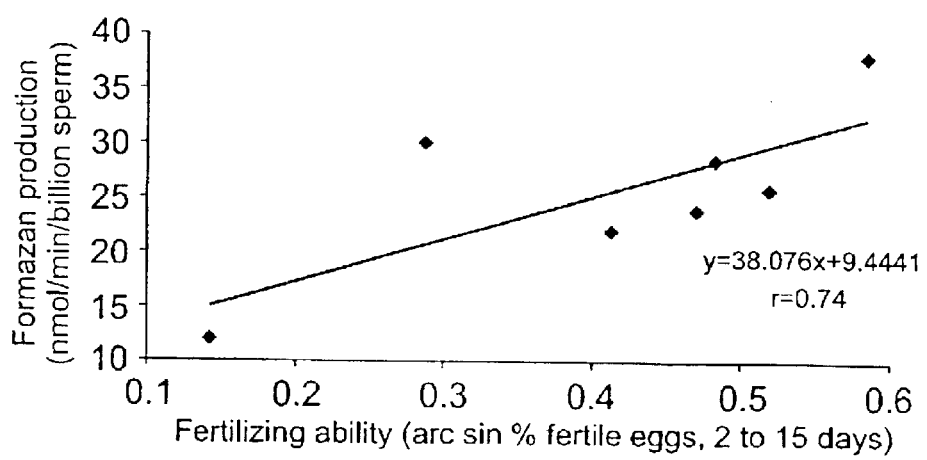
FIG. 7 shows the relationship between fertilising ability (x) measured as fertilised eggs laid by inseminated hens, expressed in Arcsin percentage values and MTT reduction potential (y) of spermatozoa from individual males. The relationship shown is y=38.08x+9.44; r=0.74; n=7.

Example 5
Comparison of Original INT-reduction Assay and MTT-reduction Assay on Same Ejaculates from Individual Male Domestic Fowl The amounts of formazan produced by reduction of INT and MTT in samples of semen from individual male domestic fowl are shown in FIG. 3 and are highly correlated. When these samples were corrected for the sperm concentration in each sample of semen, the regression equation was y=1.64x+0.19 ($R^2$=0.74) where y=MTT-formazan produced per h per million spermatozoa at 37° C. and x=INT-formazan produced per h per million spermatozoa at 20° C.

Discussion

The MTT-reduction assay of domestic fowl sperm quality has several advantages over the earlier INT-reduction assay (Chaudhuri and Wishart, 1988). The extinction coefficients are similar for both formazan pigments, but the higher incubation temperature employed in the MTT-reduction assay enables faster accumulation of reduced pigment. More importantly, the oxidoreduction potential of MTT compared to INT allows efficient MTT reduction without the need for an oxidoreduction intermediate, such as phenazine methosulphate: in the original INT assay, PMS increased the rate of formazan production nearly 3-fold (Chaudhuri and Wishart, 1988), whereas in the present work with MTT, a maximum increase of only 23% was found. Furthermore, MTT reduction seems less dependent on the blocking of cytochrome-based electron transport by cyanide, since KCN only increased the rate of MTT-formazan production by 13%, compared to 67% for INT-formazan production in the present study and 120% in a previous study (Chaudhuri and Wishart, 1988). Thus, in this study, the addition of KCN and PMS (or PES or MeoM PMS) produced only a limited increase in the reaction rate and were therefore omitted from the reagent mix with little loss of efficiency, but with elimination of the assays most unstable and toxic components.

Tetrazolium-reduction assays used for cultured cells rely on extraction of formazan pigments into organic solvents (Mossman, 1983) or the use of tetrazolium salts which produce a soluble formazan pigment such as XTT, which is released from monolayered cultured cells (Scuderio et al., 1988). When sperm suspensions are used, either system would require centrifugation to produce an optically clear sample. In embodiments of the present assays, solubilisation of the reaction mixture using e.g. SDS has the added advantage of solubilising the sperm suspension, to produce an optically clear sample without the requirement for centrifugation.

The assay is linear over 60-min incubation and over a 4-fold range of sperm concentrations (FIG. 2) which should enable comparisons of a range of samples with different sperm concentrations. Finally, the MTT-reduction assay shows good correlation with the INT-reduction assay (Chaudhuri and Wishart, 1988), which has, in turn been highly correlated with sperm motility, morphology, ATP content and fertilising ability (Chaudhuri et al, 1988). The omission of unstable and toxic reagents from the MTT-test and the elimination of the need for centrifugation to render samples optically clear for reading on a colorimeter, make the MTT assay highly amenable for application outside the laboratory.

Example 6

In the following two examples, the ability of semen to reduce MTT tetrazolium to its coloured formazan was compared with other tests of sperm quality and fertilising ability. It was found that MTT reduction was highly correlated with sperm ATP content (r=0.92); sperm mobility to penetrate Accudenz (r=0.79); sperm:perivitelline layer interaction (r=0.86) and fertilising ability (r=0.74).

Materials and Methods for Examples 6 and 7

Males were bred from commercial ISA Brown hens and were 20–28 weeks at the time of the experiments. These birds were caged individually, given a 14:10 h light:dark photoperiod and fed a commercial breeders ration ad libitum.

Semen was collected by abdominal massage (Lake, 1957), diluted 1:4 in 0.15 mol/L NaCl with 20 mmol/L TES (N-tris(hydroxymethyl)methyl, 2 aminoethane suphonic acid), pH 7.4, and incubated shaking at 22° C. for up to 1 h before assay of MTT reduction (Hazary and Wishart, 1999), ATP content (Wishart, 1982) and sperm:IPVL interaction (Robertson et al., 1998). Samples assayed by the Accudenz sperm mobility test were $5 \times 10^8$ sperm per milliliter concentration and was estimated by light scattering at 550 nm in a spectrophotometer (Proman and McLean, 1996).

Example 7

Birds were a White Leghorn type. Males were 70 weeks old and the hens were 64 weeks. Samples of semen were collected as above, diluted 1:4 in NaCl/TES and the sperm concentration calculated (as above). An insemination dose of 30 million spermatozoa from each male in 50 $\mu$l of NaCl/TES was inseminated into 10 hens. Eggs were collected and stored for up to 5 days before incubation. Fertility was estimated by candling between days 4 and 8 of incubation.

Results for Examples 6 and 7

The relationship between sperm MTT reduction potential and sperm ATP content, ability to penetrate Accudenz, hydrolytic activity towards the IPVL and fertilising ability of spermatozoa in semen samples from individual males are shown in FIGS. 4–7 respectively. These are all highly correlated.

Thus, sperm ATP and INT-reduction potential were found to be significantly correlated with the proportion of fertilised eggs laid by hens inseminated with a low dose of 10 million spermatozoa. This low dose of spermatozoa was useful to exaggerate differences in sperm fertilising ability, since the relationship between the number of inseminated spermatozoa and the proportion of fertile eggs laid by inseminated hens is saturating—so that differences in the fertilising ability of semen samples of different quality are minimised at higher insemination doses.

An alternative to 'proportion of fertilised eggs' for measuring sperm function in vivo is to measure, in the laid egg, the numbers of intravaginally-inseminated spermatozoa which reach and penetrate the perivitelline layers of the egg at fertilisation (see Wishart, 1999). This can be shown to be linearly correlated with the insemination dose of spermatozoa under conditions in which the proportion of fertile eggs is asymptotic (Wishart, 1995; Wishart and Staines, 1999) and is therefore a useful measurement for sperm function in vivo. Thus, the numbers of spermatozoa which interact with the perivitelline layers in vivo have been shown to be linearly correlated with the sperm quality test of their ability to hydrolyse the perivitelline layer in vitro, under conditions in which the relationship of these parameters with fertilising ability was asymptotic and non-linear (Robertson et al., 1998). The high correlation of MTT-reductive ability with in vitro sperm:perivitelline interaction (FIG. 3) links the former test with the above assays of sperm function in vivo.

The fertilising ability of chicken spermatozoa has been reported to be correlated with sperm motility, measured by subjective 'scoring' systems (Cooper and Rowell, 1958; Wilson et al., 1979), and by objective light-scattering techniques (Wishart and Palmer, 1986). More recently, a simple sperm mobility assay, based on the ability of spermatozoa to penetrate, and thus increase the turbidity of, solutions of the viscous polymer, Accudenz, has been applied to test poultry sperm quality (Froman and McLean, 1996). On the basis of this assay, semen from males was divided into average and high mobility groups, which differed by 10% in the proportion of fertilised eggs laid by inseminated hens (Froman et al., 1997). Our current findings, that MTT-reduction by semen from individual males is highly correlated with their ability to penetrate Accudenz, also adds credence to the value of the MTT reduction test as a predictor of domestic fowl fertilising ability.

Certain of the above parameters of individual male domestic fowl sperm quality have been demonstrated to be repeatable within different ejaculates taken from the same male and to be quantitative traits which describe a normal distribution. Furthermore, since these same studies have demonstrated up to 10-fold differences in sperm quality parameters in populations of males, these tests are valuable tools for selecting or de-selecting males to optimise fertility or cut down on the numbers of males used for breeding programmes.

Modifications and improvements can be incorporated without departing from the scope of the invention.

REFERENCES

Barbato, G. F., Cramer, P. G & Hammerstedt, R. H. (1998) A practical in vitro sperm-egg binding assay which detects subfertile males. *Biology of Reproduction* 58: 686–699.

Bilgilli, S. F., Renden, J. A. & Sexton, T. J. (1985) Fluorimetry of poultry semen: its application in the determination of viability, enzyme leakage and fertility. *Poultry Science* 64: 1227–1230.

Chaudhuri, D & Wishart, G. J. (1988) Predicting the fertilizing ability of avian semen: the development of an objective calorimetric method for assessing the metabolic activity of fowl spermatozoa. *British Poultry Science* 29: 837–845.

Chaudhuri, D., Wishart, G. J., Lake, P. E. & Ravie, O. (1988) Predicting the fertilizing ability of avian semen: a comparison of a simple calorimetric test with other methods for predicting the fertilizing ability of fowl semen. *British Poultry Science* 29: 847–851.

Cooper, D. M. & Rowell, J. G. (1958) Relations between fertility, embryonic survival and some semen characteristics in chicken. *Poultry Science* 37: 699–707.

Froman, D. P. & McLean, D. J. (1996) Objective measurement of sperm motility based upon sperm penetration of Accudenz®. *Poultry Science* 75:776–784.

Froman, D. P., Feltman, A. J. & McLean, D. J. (1997) Increased fecundity resulting from semen donor selection based upon in vitro sperm motility. *Poultry Science* 76: 73–77.

Froman, D P & Feltman, A J. (1998) Sperm mobility: a quantitative trait of the domestic fowl (*Gallus domesticus*). *Biology of Reproduction* 58: 379–384.

Lake, P. E. (1957) Fowl semen as collected by the massage method. *Journal of Agricultural Science, Cambridge* 49: 120–126.

Lake, P. E. & Stewart, J. M. (1978) Artificial insemination in poultry. *Ministry of Agriculture Fisheries and Food, Bulletin* 213. HMSO, London.

McDaniel, C. D., Hannah, J. L., Parker, H. M., Smith, T. W, Shultz, C. D. & Zumwalt C. D. (1998) Use of a sperm analyzer for evaluating broiler breeder males. 1. Effects of altering sperm quality and quantity on the sperm motility index. *Poultry Science* 77: 888–893.

Mossman, T. (1983) Rapid calorimetric assay for cellular growth and survival: application to proliferation and cytotoxic assays. *Journal of Immunological Methods* 65: 55–63.

Scuderio, D. A., Shoemaker, R. H., Paull, K. D., Monks, A., Tierney, S., Nofziger, T.H., Currens, M. J., Seniff, D. & Boyd, M. R. (1988) Evaluation of a soluble tetrazolium/formazan assay for cell growth and drug sensitivity in culture using human and other tumor cell lines. *Cancer Research* 48: 4827–4833.

Robertson, L., Wilson, Y. I., Lindsay, C. & Wishart, G. J. (1998) Evaluation of semen from individual male domestic fowl by assessment of sperm:perivitelline interaction in vitro and in vivo. *British Poultry Science* 39: 278–281.

Wilson, H. R., N. P. Piesco, E. R. Miller & W. G. Nesbeth (1979) Prediction of the fertility potential of broiler breeder males. *World's Poultry Science Journal* 35: 95–118.

Wishart, G. J. (1982) Maintenance of ATP concentrations in and of fertilising ability of fowl and turkey spermatozoa in vitro. *Journal of Reproduction and Fertility* 66: 457–462.

Wishart, G. J. (1985) Quantitation of the fertilizing ability of fresh compared with frozen and thawed fowl spermatozoa. *British Poultry Science* 26: 375–380.

Wishart, G. J. (1989) Physiological changes in fowl and turkey spermatozoa during in vitro storage. *British Poultry Science* 30: 443–454.

Wishart, G. J. (1993) Techniques for semen quality determination. *Proceedings of the 3rd International Symposium on Turkey Reproduction*, pp 83–89. Raleigh, N.C.

Wishart, G. J. (1994) Vaginal sperm transport and sperm selection. *Proceeding of the 9th European Poultry Conference*, pp 61–164. Glasgow.

Wishart, G. J. & Palmer, F. H. (1986) Correlation of the fertilizing ability of semen from individual male fowl with sperm motility and ATP content. *British Poultry Science* 27: 97–102.

Robertson, L., Wilson, Y. I., Linday, C. and Wishart, G. J. (1998) Evaluation of semen from different individual male domestic fowl by assessment of sperm:perivitelline interaction in vitro and in vivo. *British Poultry Science* 39:278–281.

Wishart, G. J. (1995). New approaches to evaluating male and female fertility, in:

Bakst, M. R. & Wishart, G. J. (Eds) *First International Symposium on the Artificial Insemination of Poultry* pp.207–223. (Illinois, USA, Poultry Science Association)

Wishart, G. J. & Palmer, F. H. (1986) Correlation of the fertilizing ability of semen from individual male fowl with sperm motility and ATP content. *British Poultry Science* 27: 97–102.

What is claimed is:

1. A method of assessing sperm quality, comprising exposing spermatozoa to the tetrazolium dye MTT to permit reduction of the MTT by the spermatozoa, solubilizing the spermatozoa to release their contents into the reaction mixture, determining the colour change in the reaction mixture as a result of the reduction of the MTT by the spermatozoa, and correlating the colour change in the reaction mixture with the quality of the sperm, wherein the spermatozoa are solubilized at a pH of 5–7.4.

2. A method as claimed in claim 1, including the step of determining the extent to which the spermatozoa reduce the MTT.

3. A method as claimed in claim 1, wherein the reaction between the spermatozoa and the MTT is carried out at 37–40° C., and at a pH within the range of pH 6–8.

4. A method as claimed in claim 1, wherein the determination of the colour change is carried out as a separate step at a lower pH than the reaction between the spermatozoa and the MTT.

5. A method as claimed in claim 1, wherein the sperm quality assessed is selected from the group of qualities consisting of viability and fertilizing ability.

6. A method as claimed in claim 1, wherein the sperm is avian sperm.

* * * * *